United States Patent
Maurin et al.

(12)

(10) Patent No.: US 6,383,996 B1
(45) Date of Patent: May 7, 2002

(54) ANTIDANDRUFF COMPOSITION FOR TREATING THE HAIR AND THE SCALP, BASED ON AN ANTIDANDRUFF AGENT AND AN ACRYLIC TERPOLYMER

(75) Inventors: Véronique Maurin, Paris; Bernard Beauquey, Clichy, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/671,196

(22) Filed: Sep. 28, 2000

(30) Foreign Application Priority Data

Sep. 29, 1999 (FR) .............................. 99 12165

(51) Int. Cl.[7] .............. C11D 3/37; C11D 3/48
(52) U.S. Cl. ............ 510/119; 510/121; 510/122; 510/123; 510/124; 510/125; 510/126; 510/127; 510/128; 510/130; 510/131; 510/382; 510/387; 510/388; 510/398; 510/477
(58) Field of Search ................. 510/119, 121, 510/122, 123, 124, 125, 126, 127, 128, 130, 131, 382, 387, 388, 398, 477

(56) References Cited

FOREIGN PATENT DOCUMENTS

| EP | 0 824 914 | | 2/1998 |
|---|---|---|---|
| EP | 824914 | * | 2/1998 |
| EP | 0 825 200 | | 2/1998 |
| FR | 2 774 901 | | 8/1999 |
| WO | 94/06403 | * | 3/1994 |

* cited by examiner

Primary Examiner—Charles Boyer
(74) Attorney, Agent, or Firm—Jacobson Holman, PLLC

(57) ABSTRACT

An antidandruff composition for treating the hair and scalp combines, in a cosmetically acceptable medium, at least one specific antidandruff agent and at least one acrylic terpolymer made up of a monomer (a) chosen from a $C_1$–$C_6$ alkyl acrylate and a $C_1$–$C_6$ alkyl methacrylate; a monomer (b) chosen from a heterocyclic vinyl compound containing at least one nitrogen or sulphur atom, a (meth)acrylamide, a mono- or di($C_1$–$C_4$)alkylamino($C_1$–$C_4$)alkyl (meth)acrylate, and a mono- or di($C_1$–$C_4$)alkylamino($C_1$–$C_4$)alkyl(meth)acrylamide, a monomer (c) chosen from a urethane produced by reaction between a monoethylenic unsaturated isocyanate and a nonionic surfactant, a copolymerizable ethylenic surfactant monomer, a surfactant monomer of urea type, an allyl ether containing alkylenoxy groups, and a nonionic monomer of urethane type.

38 Claims, No Drawings

ANTIDANDRUFF COMPOSITION FOR TREATING THE HAIR AND THE SCALP, BASED ON AN ANTIDANDRUFF AGENT AND AN ACRYLIC TERPOLYMER

The present invention relates generally to antidandruff compositions for treating the hair and the scalp, based on an antidandruff agent and an acrylic terpolymer, as well as to a treatment process using these compositions.

Desquamative disorders of the scalp, such as dandruff are linked to the presence of a characteristic yeast known as Malassezia ovalis, this yeast previously being known as Pityrosporum (P. ovale and P. orbiculare). The usual treatment for dandruff involves using antidandruff agents, in particular antifungal and/or antibacterial agents in a medium, such as a shampoo, a gel or a lotion, which is capable of distributing these agents and depositing them on the teguments.

It has been found that treatments using these antidandruff agents often have the drawback of adversely affecting keratin fibres, more particularly sensitized keratin fibres, thus reducing their cosmetic performance qualities, in particular making them coarser and more charged.

There is thus a need for an antidandruff cosmetic composition such as, for example, a Shampoo, a lotion or a gel, which gives acceptable cosmetic performance qualities, in particular as regards the softness of the hair.

A subject of the present invention is antidandruff compositions for treating the hair and the scalp, which give the hair the same cosmetic properties as those obtained during the use of a composition for treating keratin materials which does not comprise antidandruff agent.

The Applicant has discovered, surprisingly, that it is possible to formulate compositions for treating keratin materials, in particular lotions and shampoos, having the desired properties, by using in these compositions an antidandruff agent combined with a specific acrylic terpolymer defined below. Specifically, it has been found that the use of compositions of the present invention improves the cosmetic properties of the hair and the scalp, particularly by giving wet sensitized hair greater softness and suppleness and by giving dried hair greater softness and smoothness. The use of the compositions of the invention also gives a head of hair which has a smoother appearance.

It has also been found that the combinations of the invention have good skin tolerance and make it easier to disentangle dried hair.

Other subjects of the invention will become apparent in the light of the description and the examples which follow.

According to the invention, the antidandruff compositions for treating the hair and the scalp are essentially characterized in that they comprise, in a cosmetically acceptable medium, at least one specific antidandruff agent defined below and at least one acrylic terpolymer consisting of:
from 5% to 80% by weight, preferably from 15% to 70% by weight and more preferably from 40% to 70% by weight of an acrylate monomer (a) chosen from a $C_1$–$C_6$ alkyl acrylate and a $C_1$–$C_6$ alkyl methacrylate;
from 5% to 80% by weight, preferably from 10% to 70% by weight and more preferably from 20% to 60% by weight, of a monomer (b) chosen from a heteroylic vinyl compound containing at least one nitrogen or sulphur atom, a (meth)acrylamide, a mono- or di($C_1$–$C_4$)alkylamino($C_1$–$C_4$)alkyl (meth)acrylate and a mono- or di ($C_1$–$C_4$) alkylamino ($C_1$–$C_4$) alkyl (meth) acrylamide;
from 0.1% to 30% by weight, preferably from 0.1% to 10% by weight, of a monomer (c) chosen from:

a urethane produced by reaction between a monoethylenic unsaturated isocyanate and a nonionic surfactant comprising a block copolymer of 1,2-butylene oxide and of ethylene oxide with a $C_{1-4}$ alkoxy end;
a copolymerizable ethylenic unsaturated surfactant monomer obtained by condensation of a nonionic surfactant with an α, β-ethylenic unsaturated carboxylic acid or its anhydride;
a surfactant monomer chosen from the products of reaction of the type such as a urea of a monoethylenic unsaturated monoisocyanate with a nonionic surfactant containing an amine function;
a (meth)allyl ether of formula $CH_2=CR_1CH_2OA_mB_nA_pR_2$ in which $R_1$ denotes a hydrogen atom or a methyl group, denotes a propylenoxy or butylenoxy group, B denotes ethylenoxy, n is equal to zero or denotes an integer less than or equal to 200 and preferably less than or equal to 100, m and p denote zero or an integer less than n and $R_2$ is a hydrophobic group of at least 8 carbon atoms and preferably of $C_8$–$C_{30}$; and a nonionic monomer of urethane type produced by reaction of a monohydric nonionic surfactant with a monoethylenic unsaturated isocyanate;
the weight percentages of monomers being based on the total weight of the monomers constituting the terpolymer.

According to one embodiment of the invention, the acrylic terpolymer is present in a proportion of from 0.01% to 20% by weight of active material (A.M.), preferably 0.1% to 10% by weight, relative to the total weight of the composition.

Acrylate monomers (a) that are preferred in particular comprise $C_2$–$C_6$ alkyl acrylates. Ethyl acrylate is most particularly preferred.

Examples of preferred monomers (b) which should be mentioned are N,N-dimethylaminoethyl methacrylate (DMAEMA), N,N-diethylaminoethyl acrylate, N,N-diethylaminoethyl methacrylate, N-t-butylaminoethyl acrylate, N-t-butylaminoethyl methacrylate, N,N-dimethylaminopropylacrylamide, N,N-dimethylaminopropylmethacrylamide, N,N-diethylaminopropylacrylamide and N,N-diethylaminopropylmethacrylamide. N,N-Dimethylaminoethyl methacrylate is most particularly preferred.

The preferred monomers (c) are the copolymerizable ethylenic unsaturated surfactant monomers obtained by condensing a nonionic surfactant with an α,β-ethylenic unsaturated carboxylic acid or its anhydride, preferably $C_3$–$C_4$ mono- or dicarboxylic acids or their anhydrides and more particularly acrylic acid, methacrylic acid, crotonic acid, maleic acid, maleic anhydride and most particularly itaconic acid and itaconic anhydride.

The monomers (c) that are particularly preferred correspond to the copolymerizable ethylenic unsaturated surfactant monomers obtained by condensing a nonionic surfactant with itaconic acid. Among the nonionic surfactants which may be mentioned in particular are $C_{10}$-$C_{30}$ fatty alcohols alkoxylated with 2 to 100 mol and preferably from 5 to 50 mol of an alkylene oxide, such as, for example, polyethylene glycol ethers of $C_{10}$–$C_{30}$ fatty alcohols and more particularly the polyethylene glycol ethers of cetyl alcohol which are known as Ceteth in the CTFA dictionary, 7th edition, 1997.

Conventional methods for preparing these acrylic terpolymers are known to those skilled in the art. Such methods include solution polymerization, precipitation polymerization and emulsion polymerization, for example. Terpolymers in accordance with the invention and methods for preparing them are described in particular in patent applications EP-A-0 824 914 and EP-A-0 825 200.

Among these terpolymers, it is preferred in particular to use the <<Structure® Plus>> polymer sold by the company National starch, which consists of acrylates, amino (meth) acrylates and $C_{10}$–$C_{30}$ alkyl itaconate, polyoxyethylenated with 20 mol of ethylene oxide, in the form of an aqueous dispersion containing 20% A.M.

In addition to these monomers, the terpolymer can contain other monomers which allow the said terpolymer to be crosslinked. These monomers are used in relatively low proportions, of up to 2% by weight relative to the total weight of the monomers used to prepare the terpolymer. Such crosslinking monomers comprise aromatic monomers bearing several vinyl substituents, alicyclic monomers bearing several vinyl substituents, bifunctional esters of phthalic acid, bifunctional esters of methacrylic acid, multifunctional esters of acrylic acid, N-methylenebisacrylamide and aliphatic monomers bearing several vinyl substituents such as dienes, trienes and tetraenes. Crosslinking monomers may be, in particular, divinylbenzenes, trivinylbenzenes, 1,2,4-trivinyl-cyclohexene, 1,5-hexadiene, 1,5,9-decatriene, 1,9-decadienes, 1,5-heptadienes, diallyl phthalates, ethylene glycol dimethacrylate, polyethylene glycol dimethacrylate, penta- and tetraacrylates, triallyl pentaerythritols, octaallyl sucroses, cycloparaffins, cycloolefins and N-methylenebisacrylamide.

The antidandruff agent in the compositions of the present invention is chosen from:

1) benzethonium chloride, benzalkonium chloride, chlorhexidine, chloramine T, chloramine B, 1,3-dibromo-5,5-dimethylhydantoin, 1,3-dichloro-5,5-dimethyl-hydantoin, 3-bromo-1-chloro-5,5-dimethylhydantoin and N-chlorosuccinimide;

2) the 1-hydroxy-2-pyridone derivatives represented by formula (I):

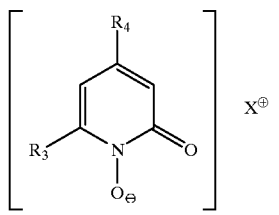

(I)

in which $R_3$ represents an alkyl group containing from 1 to 17 carbon atoms, an alkenyl group containing from 2 to 17 carbon atoms, a cycloalkyl group containing from 5 to 8 carbon atoms or a bicycloalkyl group containing from 7 to 9 carbon atoms; a cycloalkyl(-alkyl) group, an aryl group, an aralkyl group with an alkyl containing from 1 to 4 carbon atoms, an arylalkenyl group with an alkenyl containing from 2 to 4 carbon atoms, an aryloxyalkyl or arylmercaptoalkyl group with an alkyl containing from 1 to 4 carbon atoms, a furylalkenyl group with an alkenyl or a furyl containing from 2 to 4 carbon atoms, an alkoxy group containing from 1 to 4 carbon atoms, a nitro group, a cyano group or a halogen atom, $R_4$ represents a hydrogen atom, a $C_1$–$C_4$ alkyl group, a $C_2$–$C_4$ alkenyl group, a halogen atom, a phenyl group or a benzyl group; X represents an organic base, an alkali metal ion, an alkaline-earth metal ion or an ammonium ion.

Compounds of formula (I) are, for example, 1-hydroxy-4-methyl-2-pyridone, 1-hydroxy-6-methyl-2-pyridone, 1-hydroxy-4,6-dimethyl-2-pyridone, 1-hydroxy-4-methyl-6-(2,4,4-trimethylpentyl)-2-pyridone, 1-hydroxy-4-methyl-6-cyclohexyl-2-pyridone, 1-hydroxy-4-methyl-6-(methylcyclohexyl)-2-pyridone, 1-hydroxy-4-methyl-6-2-bicyclo[2,2,1]heptyl)-2-pyridone, 1-hydroxy-4-methyl-4-(4-methylphenyl)-2-pyridone, 1-hydroxy-4-methyl-6-[1-(4-nitrophenoxy)butyl]-2-pyridone, 1-hydroxy-4-methyl-6-(4-cyanophenoxymethyl)-2-pyridone, 1-hydroxy-4-methyl-6-(phenylsulphonylmethyl)-2-pyridone and 1-hydroxy-4-methyl-6-(4-bromobenzyl)-2-pyridone.

A compound of formula (I) which is particularly preferred is the one for which $R_3$ denotes the radical

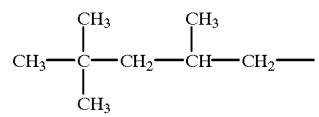

and $R_4$ denotes methyl and $X^+$ denotes $N^+H_3CH_2CH_2OH$.

This compound is sold, for example, under the name Octopirox (1-hydroxy-4-methyl-6-(2,4,4-trimethylpentyl)-2-pyridone, monoethanolamine salt) by the company Hoechst.

3) the trihalocarbamides of formula (II) below:

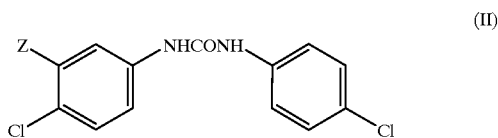

(II)

in which Z represents a halogen atom such as chlorine or a $C_1$–$C_4$ trihaloalkyl group such as $CF_3$;

4) triclosan, represented by formula (III)

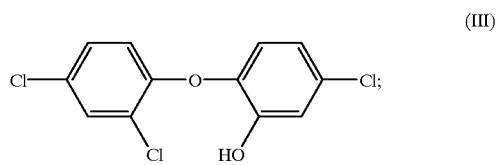

(III)

5) azole compounds such as climbazole, ketoconazole, clotrinazole, econazole, isoconazole and miconazole;

6) antifungal polymers such as amphotericin B or nystatin;

7) selenium sulphides;

8) other antidandruff agents are sulphur in its various forms, cadmium sulphide, allantoin, coal tar or wood tar and derivatives thereof, in particular cade oil, undecylenic acid, fumaric acid, and allylamines such as terbinafine;

9) or a mixture of these antidandruff agents.

The antidandruff agents mentioned above can also, where appropriate, be used in the form of their addition salts with physiologically acceptable acids, in particular in the form of salts with sulphuric, nitric, thiocyanic, hydrochloric, hydrobromic, hydroiodic, phosphoric, acetic, benzoic, glycolic, aceturic, succinic, nicotinic, tartaric, maleic, palmitic, methanesulphonic, propanoic, 2-oxopropanoic, propanedioic, 2-hydroxy-1,4-butanedioic, 3-phenyl-2- propenoic, α-hydroxybenzeneacetic, ethanesulphonic, 2-hydroxyethanesulphonic, 4-methylbenzenesulphonic, 4-amino-2-hydroxybenzoic, 2-phenoxybenzoic, 2-acetyloxybenzoic, picric, lactic, citric, malic or oxalic acid and amino acids.

The antidandruff agents mentioned above can also, where appropriate, be used in the form of their addition salts with physiologically acceptable organic or inorganic bases. Examples of organic bases are, in particular, alkanolamines of low molecular weight, such as ethanolamine, diethanolamine, N-ethylethanolamine, triethanolamine, diethylaminoethanol and 2-amino-2-methylpropanedione; non-volatile bases such as ethylenediamine, hexamethylenediamine, cyclohexylamine, benzylamine and N-methylpiperazine; quaternary ammonium hydroxides, for example trimethylbenzyl hydroxide; guanidine and its derivatives, and in particular its alkyl derivatives. Examples of inorganic bases are, in particular, alkali metal salts, such as sodium or potassium salts; ammonium salts, alkaline-earth metal salts, such as magnesium and calcium salts; salts of cationic di-, tri- or tetravalent metals, such as zinc, aluminium and zirconium. Alkanolamines, ethylenediamine and inorganic bases such as alkali metal salts are preferred.

The antidandruff agents are present in proportions in particular of between 0.001% and 10% by weight relative to the total weight of the composition and preferably in proportions of between 0.01% and 5% by weight relative to the total weight of the composition.

The compositions according to the invention preferably also contain at least one surfactant, chosen in particular from anionic, amphoteric, nonionic and cationic surfactants and mixtures thereof.

Among the anionic surfactants which may be mentioned are alkaline salts, ammonium salts, amine salts, amino alcohol salts and magnesium salts of the following compounds: alkyl sulphates, alkyl ether sulphates, alkylamido ether sulphates, alkylaryl polyether sulphates, monoglyceride sulphates; alkyl sulphonates, alkylamide sulphonates, alkylaryl sulphonates, olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl phosphates, alkyl ether phosphates; acyl sarcosinates, acyl isethionates and N-acyl taurates.

The alkyl or acyl radical in these various compounds generally consists of a carbon-based chain containing from 8 to 30 carbon atoms.

Among the anionic surfactants which may also be mentioned are fatty acid salts such as oleic, ricinoleic, palmitic and stearic acid salts; coconut oil acid or hydrogenated coconut oil acid; acyl lactylates, in which the acyl radical contains from 8 to 30 carbon atoms.

Surfactants considered as weakly anionic can also be used, such as polyoxyalkylenated carboxylic alkyl or alkylaryl ether acids or salts thereof, polyoxyalkylenated carboxylic alkylamido ether acids or salts thereof, and alkyl D-galactosiduronic acids or salts thereof.

The nonionic surfactants are chosen more particularly from polyethoxylated, polypropoxylated or polyglycerolated fatty acids or alkylphenols or alcohols, with a fatty chain containing 8 to 30 carbon atoms, the number of ethylene oxide or propylene oxide groups being between 2 and 50 and the number of glycerol groups being between 2 and 30.

Mention may also be made of copolymers of ethylene oxide and propylene oxide; condensates of ethylene oxide and of propylene oxide with fatty alcohols; polyethoxylated fatty amides preferably containing 2 to 30 mol of ethylene oxide; polyglycerolated fatty amides preferably comprising 1 to 5 and in particular 1.5 to 4 glycerol groups; polyethoxylated fatty amines preferably containing 2 to 30 mol of ethylene oxide; oxyethylenated fatty acid esters of sorbitan with 2 to 30 mol of ethylene oxide; fatty acid esters of sucrose, fatty acid esters of polyethylene glycol, alkylpolyglycosides, carbamate or amide derivatives of N-alkylglucamines, aldobionamides, amine oxides such as alkylamine oxides or of N-acylamidopropylmorpholine.

The preferred amphoteric surfactants are secondary or tertiary aliphatic amine derivatives, in which the aliphatic radical is a linear or branched chain containing 8 to 22 carbon atoms and which contains at least one carboxylate, sulphonate, sulphate, phosphate or phosphonate water-solubilizing anionic group; $(C_8-C_{20})$ alkylbetaines, sulphobetaines, $(C_8-C_{20})$ alkyl-amido $(C_1-C_6)$ alkylbetaines or $(C_8-C_{20})$ alkyl-amido $(C_1-C_6)$ alkylsulphobetaines.

Among the amine derivatives which may be mentioned are the products sold under the name Miranol, such as those described in patents U.S. Pat. No. 2 528 378 and 2 781 354 and classified in the CTFA dictionary, 7th edition, 1997, under the name Disodium Cocoamphodiacetate, Disodium Lauroamphodiacetate, Disodium Capryloamphodiacetate, Disodium Capro-amphodiacetate, Disodium Cocoamphodipropionate, Disodium Lauroamphodipropionate, Di sodium Caproamphodipropionate, Disodium Capryloamphodipropionate, Lauroamphodipropionate acid, Cocoamphodipropionate acid.

The cationic surfactants are chosen in particular from optionally polyoxyalkylenated primary, secondary or tertiary fatty amine salts; quaternary ammonium salts; imidazoline derivatives; or amine oxides of cationic nature.

The preferred quaternary ammonium salts are tetraalkylammonium halides (for example chlorides) such as, for example, dialkyldimethylammonium or alkyltrimethylammonium chlorides, in which the alkyl radical contains from about 12 to 22 carbon atoms, in particular behenyltrimethylammonium, distearyldimethylammonium, cetyltrimethylammonium or benzyldimethylstearylammonium chloride or alternatively the stearamidopropyldimethyl (myristyl acetate)ammonium chloride sold under the name <<Cepharyl 70>> by the company Van Dyk.

Diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts (chlorides or methyl sulphate in particular) and mixtures thereof can also be used. The acyl radicals preferably contain 14 to 18 carbon atoms and are more particularly obtained from a plant oil such as palm oil or sunflower oil.

Preferably, at least one detergent surfactant is used, in particular if it is desired to obtain antidandruff shampoos.

The surfactants are optionally used in the compositions in accordance with the invention in proportions of between 0.01% and 50% by weight, relative to the total weight of the composition. When the compositions are in the form of shampoos, they are generally used in a proportion of at least 4% by weight, preferably between 5% and 50% by weight, relative to the total weight of the composition and in particular between 8% and 35%.

The compositions according to the invention have a pH generally of between 3 and 12 and more particularly between 4 and 8.

The cosmetically acceptable medium for the compositions consists either of water or of one or more solvents or of a mixture of water and at least one cosmetically acceptable solvent chosen from lower alcohols, alkylene glycols and polyol ethers.

In one preferred embodiment of the invention, the compositions according to the present invention contain modified or unmodified polyorganosiloxanes, i.e. polyorganosiloxane oils or polyorganosiloxane gums or resins, in their native form or in the form of solutions in organic solvents or alternatively in the form of emulsions or microemulsions.

Among the polyorganosiloxanes which may be used in accordance with the present invention, mention may be made, in a non-limiting manner, of:

I. Volatile silicones: these have a boiling point of between 60° C. and 260° C. They are chosen from cyclic silicones containing from 3 to 7 and preferably 4 to 5 silicon atoms. Examples of these are octamethylcyclotetrasiloxane sold under the name <<Volatile Silicone 7207" by Union Carbide or <<Silbione 70045 V2" by Rhône-Poulenc, decamethylcyclopentasiloxane sold under the name <<Volatile Silicone 715811" by Union Carbide, <<Silbione 70045 V5" by Rhône-Poulenc, as well as mixtures thereof. Mention is also made of cyclocopolymers such as dimethylsiloxane/methylalkylsiloxane, for instance <<Volatile Silicone FZ3109" sold by the company Union Carbide, which is a dimethylsiloxane/methyloctylsiloxane cyclocopolymer.

II. Non-volatile silicones: these consist mainly of:
(i) polyalkylsiloxanes; among the polyalkylsiloxanes which may mainly be mentioned are linear polydimethylsiloxanes containing trimethylsilyl end groups, such as, for example, and in a non-limiting manner, the <<Silbione>> oils of the 70047 series sold by Rhodia Chimie; the $DC_{200}$ oils from Dow Corning and PDMSs containing hydroxydimethylsilyl end groups;
(ii) polyarylsiloxanes;
(iii) polyalkylarylsiloxanes; mention may be made of linear and branched polymethylphenylsiloxanes, polydimethylmethylphenylsiloxanes and polydimethyldiphenylsiloxanes, such as, for example, the oil <<Rhodorsil 76311 from Rhodia Chimie;
(iv) silicone gums; these are polydiorganosiloxanes with a molecular mass of between 200,000 and 5,000,000, which are used alone or as a mixture in a solvent chosen from volatile silicones, polydimethylsiloxane (PDMS) oils, polyphenylmethylsiloxane (PPMS) oils, isoparaffins, methylene chloride, pentane, dodecane, tridecane, tetradecane or mixtures thereof; mention is made, for example, of the following compounds:
polydimethylsiloxane,
poly[(dimethylsiloxane)/(methylvinylsiloxane)],
poly[(dimethylsiloxane)/(diphenylsiloxane)],
poly[(dimethylsiloxane)/(phenylmethylsiloxane)],
poly[(dimethylsiloxane)/(diphenylsiloxane)/(methylvinylsiloxane)];
mention may also be made, for example, in a non-limiting manner, of the following mixtures:
1) mixtures formed from a polydimethylsiloxane hydroxylated at the end of a chain (Dimethiconol according to the CTFA nomenclature) and from a cyclic polydimethylsiloxane (Cyclomethicone according to the CTFA nomenclature), such as the product <<Q2 1401>> sold by the company Dow Corning;
2) mixtures formed from a polydimethylsiloxane gum with a cyclic silicone, such as the product <<SF 1214 Silicone Fluid>> from General Electric, which is an SE 30 gum of MW 500,000 dissolved in <<SF 1202 Silicone Fluid>> (decamethylcyclopentasiloxane);
3) mixtures of two PDMSs of different viscosity, in particular of a PDMS gum and of a PDMS oil, such as the products <<SF 1236>> and <<CF 1241>> from the company General Electric;

(v) silicone resins; preferably crosslinked siloxane systems containing $R_2SiO_{2/2}$, $RSiO_{3/2}$ and $Si_{4/2}$ units in which R represents a hydrocarbon group containing 1 to 6 carbon atoms or a phenyl group. Among these resins, mention may be made of the product sold under the name <<Dow Corning 593>>;

(vi) organomodified polyorganosiloxanes; i.e. silicones as defined above, comprising in their general structure one or more organofunctional groups directly linked to the siloxane chain or linked via a hydrocarbonbased radical; mention is made, for example, of silicones comprising:
a) polyethylenoxy and/or polypropylenoxy groups optionally comprising alkyl groups, such as the product known as dimethicone copolyol, sold by the company Dow Corning under the name <<DC 1248", and alkyl ($C_{12}$) methicone copolyol sold by the company Dow Corning under the name <<Q2 5200";
b) (per)fluoro groups such as trifluoroalkyl groups, such as, for example, those sold by the company General Electric under the names <<FF.150 Fluorosilicone Fluid>>;
c) hydroxyacylamino groups, such as those described in European patent application EP-A-0 342 834, and in particular the silicone sold by the company Dow Corning under the name <<Q2-8413";
d) thiol groups, such as the silicones <<X 2-8360" from Dow Corning or <<GP 72A>> and <<GP 71" from Genesee;
e) substituted or unsubstituted amine groups, such as the products sold under the name GP 4 Silicone Fluid and GP 7100 by the company Genesee, or the products sold under the names Q2 8220 and Dow Corning 929 or 939 by the company Dow Corning. The substituted amine groups are, in particular, $C_1$–$C_4$ aminoalkyl or amino ($C_1$–$C_4$) alkylamino ($C_1$–$C_4$)alkyl groups. The silicones known as amodimethicone and trimethylsilylamodimethicone according to the CTFA name (1997) are used more particularly;
f) carboxylate groups, such as the products described in European patent EP 186 507 from Chisso Corporation;
g) hydroxyl groups, such as the polyorganosiloxanes containing a hydroxyalkyl function, described in patent application FR-A-2 589 476;
h) alkoxy groups containing at least 12 carbon atoms, such as the product <Silicone Copolymer F 755" from SWS Silicones;
i) acyloxyalkyl groups containing at least 12 carbon atoms, such as, for example, the polyorganosiloxanes described in patent application FR-A-2 641 185;
j) quaternary ammonium groups, such as in the product <<Abil K 32701" from the company Goldschmidt;
k) amphoteric or betaine groups, such as in the product sold by the company Goldschmidt under the name <<Abil B 9950";
l) bisulphite groups, such as in the products sold by the company Goldschmidt under the names <<Abil S 201" and <<Abil S 255";

(vii) block copolymers containing a linear polysiloxane-polyalkylene block as repeating unit; the preparation of such block copolymers used in the context of the present invention is described in European patent application EP 0 492 657 A1, the teaching of which is included by way of reference in the present description;

(viii) grafted silicone polymers, containing a non-silicone organic skeleton, consisting of a main organic chain formed from organic monomers containing no silicone, onto which is grafted, within the said chain as well as, optionally, on at least one of its ends, at least one polysiloxane macromonomer; in particular those chosen more preferably from those described in U.S. Pat. Nos. 4 963 935, 4 728 571 and 4 972 037 and patent applications EP-A-0 412 704, EP-A-0 412 707, EP-A-0 640 105 and WO 95/00578, the teachings of which are included in their entirety in the present description by way of non-limiting references;

(ix) grafted silicone polymers, containing a polysiloxane skeleton grafted with non-silicone organic monomers, comprising a main polysiloxane chain onto which is grafted, within the said chain as well as, optionally, on at least one of its ends, at least one organic macromonomer containing no silicone; examples of such polymers, and the particular method for preparing them, are described in particular in patent applications EP-A-0 582 152, WO 93/23009 and WO 95/03776, the teachings of which are included in their entirety in the present description by way of non-limiting references;

(x) or mixtures thereof.

The polyorganosiloxanes preferably used according to the invention are non-volatile polyorganopolysiloxanes and preferably polydimethylsiloxane oils or gums that are optionally aminated, arylated or alkylarylated.

The polyorganosiloxanes are used in the compositions of the invention in proportions of between 0.01% and 20% by weight and preferably between 0.1 and 10% by weight, relative to the total weight of the composition.

In another preferred embodiment, the compositions of the invention also contain at least one cationic polymer chosen from all those already known per se, in particular those described in patent application EP-A-0 337 354 and in French patent applications FR-A-2 270 846, 2 383 660, 2 598 611, 2 470 596 and 2 519 863.

The cationic polymers used generally have a molecular mass of between 500 and $5 \cdot 10^6$ approximately and preferably between $10^3$ and $3 \cdot 10^6$ approximately.

Among the cationic polymers which may be mentioned are guaternized proteins (or protein hydrolysates) and polymers of the polyamine, polyaminoamide and polyquaternary ammonium type. These are known products.

The quaternized proteins or protein hydrolysates are in particular chemically modified polypeptides bearing quaternary ammonium groups at the end of a chain, or grafted onto this chain. Their molecular mass can vary, for example, from 1500 to 10,000, and in particular from 2000 to 5000 approximately. Among these compounds, mention may be made in particular of:

collagen hydrolysates bearing triethylammonium groups, such as the products known in the CTFA dictionary as <<Triethonium Hydrolysed Collagen Ethosulphate>>;

collagen hydrolysates bearing trimethylammonium chloride and trimethylstearylammonium chloride groups, which are known in the CTFA dictionary as <<Steartrimonium Hydrolysed Collagen>>;

protein hydrolysates bearing on the polypeptide chain quaternary ammonium groups comprising at least one alkyl radical containing from 1 to 18 carbon atoms.

Among these protein hydrolysates which may be mentioned, inter alia, are <<Croquat L>>, <<Croquat M>>, <<Croquat S>> and <<Crotein Q>> sold by the company Croda.

Other quaternized proteins or hydrolysates are, for example, those sold by the company Inolex, under the name Lexein QX 3000>>.

Mention may also be made of quaternized plant proteins such as wheat, corn or soybean proteins: quaternized wheat proteins which may be mentioned are those known in the CTFA dictionary as <<Cocodimonium Hydrolysed Wheat Protein>>, <<Lauridimonium Hydrolysed Wheat Protein>> or <<Steardimonium Hydrolysed Wheat Protein>>.

The polymers of the polyamine, polyaminoamide or polyquaternary ammonium type which may be used in accordance with the present invention and which may be mentioned in particular are those described in French patents Nos. 2 505 348 and 2 542 997. Among these polymers, mention may be made of:

(1) Quaternized or non-quaternized vinylpyrrolidone/dialkylaminoalkyl acrylate or methacrylate copolymers, such as the polymers described in detail in French patents 2 077 143 and 2 393 573.

(2) Cellulose ether derivatives comprising quaternary ammonium groups, described in French patent 1 492 597.

(3) Cationic cellulose derivatives such as cellulose copolymers or cellulose derivatives grafted with a water-soluble quaternary ammonium monomer, and described in particular in US patent 4 131 576, such as hydroxyalkylcelluloses, for instance hydroxymethyl-, hydroxyethyl- or hydroxypropylcelluloses grafted in particular with a methacryloylethyltrimethylammonium, methacrylamidopropyltrimethylammonium or dimethyldiallylammonium salt.

(4) Polysaccharides and in particular cationic guar gums described more particularly in U.S. Pat. Nos. 3 589 578 and 4 031 307.

(5) Polymers consisting of piperazinyl units and of divalent alkylene or hydroxyalkylene radicals containing straight or branched chains, optionally interrupted with oxygen, sulphur or nitrogen atoms or with aromatic or heterocyclic rings, as well as the oxidation and/or quaternization products of these polymers. Such polymers are described in particular in French patents 2 162 025 and 2 280 361.

(6) Water-soluble polyaminoamides prepared in particular by polycondensation of an acidic compound with a polyamine; these polyaminoamides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or with an oligomer resulting from the reaction of a bifunctional compound which is reactive towards a bis-halohydrin, a bis-azetidinium, a bis-haloacyldiamine, a bis-alkyl halide, an epihalohydrin, a diepoxide or a bis-unsaturated derivative, the crosslinking agent being used in proportions ranging from 0.025 to 0.35 mol per amine group of the polyaminoamide; these polyaminoamides can be alkylated or, if they comprise one or more tertiary amine functions, they can be quaternized. Such polymers are described in particular in French patents 2 252 840 and 2 368 508.

(7) Polyaminoamide derivatives resulting from the condensation of polyalkylene polyamines with polycarboxylic acids followed by an alkylation with bifunctional agents. Mention may be made, for example, of adipic acid/dialkylaminohydroxyalkyldialkylenetriamine polymers in which the alkyl radical contains from 1 to 4 carbon atoms and preferably denotes methyl, ethyl or propyl. Such polymers are described in particular in French patent 1 583 363.

(8) Polymers obtained by reacting a polyalkylene polyamine comprising two primary amine groups and at least one secondary amine group with a dicarboxylic acid chosen from diglycolic acid and saturated aliphatic dicarboxylic acids containing from 3 to 8 carbon atoms, the Molar ratio between the polyalkylene polyamine and the dicarboxylic acid being between 0.8:1 and 1.4:1, the polyaminoamide resulting therefrom being reacted with the epichlorohydrin in a molar ratio of epichlorohydrin relative to the secondary amine group of the polyaminoamide of between 0.5:1 and 1.8:1. Such polymers are described in particular in U.S. Pat. Nos. 3 227 615 and 2 961 347.

(9) Cyclopolymers of methyldiallylamine or of dimethyldiallylammonium, in particular those described in French patent 2 080 759 and in its Certificate of Addition 2 190 406.

(10) The diquaternary ammonium polymers described in French patents 2 320 330, 2 270 846, 2 316 271, 2 336 434 and 2 413 907 and U.S. Pat. Nos. 2 273 780, 2 375 853, 2 388 614, 2 454 547, 3 206 462, 2 261 00.2, 2 271 378, 3 874 870, 4 001 432, 3 929 990, 3 966 904, 4 005 193, 4 025 617, 4 025 627, 4 025 653, 4 026 945 and 4 027 020.

(11) The polyquaternary ammonium polymers described in particular in patent application EP-A-122324.

(12) Homopolymers or copolymers derived from acrylic or methacrylic acids and comprising $CH_2$—$CHR_a$—$CO$—$O$—$_1$—$NR_eR_f$, $CH_2$—$CHR_a$—$CO$—$O$—$A_1$—$N^+R_bRR_cR_d$, $X^-$ and/or $CH_2$—$CHR_a$—$CO$—$NH$—$A_1$—$N^+R_bR_cR_d$, $X^-$ units, in which the groups $R_a$ independently denote H or $CH_3$, the groups $A_1$, independently denote a linear or branched alkyl group of 1 to 6 carbon atoms or a hydroxyalkyl group of 1 to 4 carbon atoms, the groups $R_b$, $P_c$ and $R_d$, which may be identical or different, independently denote an alkyl group of 1 to 18 carbon atoms or a benzyl radical, the groups $R_e$ and $R_f$ represent a hydrogen atom or an alkyl group of 1 to 6 carbon atoms, $X^{31}$ denotes an anion, for example methosulphate or halide, such as chloride or bromide,

(13) Quaternary polymers of vinylpyrrolidone and of vinylimidazole such as, for example, the products sold under the names <<Luviquat FC 905>>, <<Luviquat FC 550>> and <<Luviquat FC 370>> by the company BASF.

(14) The polyamines such as <<Polyquart H>> sold by Henkel, referred to under the name <<Polyethylene Glycol Tallow Polyamine>> in the CTFA dictionary.

(15) Crosslinked polymers of methacryloyloxyethyltrimethylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by a crosslinking with a compound containing olefinic unsaturation, in particular methylenebisacrylamide. An acrylamide/methacryloyloxyethyltrimethylammonium chloride crosslinked copolymer (20/80 by weight) in the form of a dispersion containing 50% by weight of the said copolymer in mineral oil can more particularly be used.

Other cationic polymers which can be used in the context of the invention are polyalkyleneimines, in particular polyethyleneimines, polymers containing vinylpyridine or vinylpyridinium units, condensates of polyamines and of epichlorohydrin, polyquaternary ureylenes and chitin derivatives.

Among all the cationic polymers which can be used in the context of the present invention, cellulose ether derivatives comprising quaternary ammonium groups, polysaccharides and in particular cationic guar gum and cyclopolymers of methyldiallylamine or of dimethyldiallylammonium are preferred.

The cationic polymers are used in the compositions of the invention in proportions of between 0.001% and 20% by weight and preferably between 0.05% and 5% by weight, relative to the total weight of the composition.

The compositions according to the invention can furthermore also contain at least one adjuvant chosen from the adjuvants usually used in cosmetics, such as fragrances, preserving agents, sequestering agents, wetting agents, sugars, plant, animal, mineral or synthetic oils, amphoteric polymers, menthol, nicotinate derivatives, agents for preventing hair loss, foam stabilizers, propellants, dyes, ceramides, vitamins or provitamins, acidifying or basifying agents or other well-known cosmetic adjuvants.

In one preferred embodiment of the invention, the compositions according to the invention are used as shampoos for washing and treating the hair and the scalp. They can also be used as antidandruff lotions or antidandruff conditioners.

The hair treatment process consists in applying a composition as defined above to wet or dry hair in effective amounts, this application optionally being followed by rinsing after the composition has optionally been left on the hair for a period of time.

The examples which follow are intended to illustrate the invention.

| EXAMPLE I: ANTIDANDRUFF SHAMPOO | |
|---|---|
| Glycol distearate | 2 g |
| Sodium N-cocoylamidoethyl-N-ethoxycarboxymethyl glycinate containing 38% A.M., sold under the name <<Miranol C2M conc.>> by the company Rhodia Chimie | 2 g |
| Cocoyl betaine as an aqueous 30% solution, sold under the name <<Dehyton AB 30>> by the company Henkel | 4 g |
| Compound sold under the name <<Octopirox>> by the company Hoechst | 2 g |
| Hydroxyethylcellulose crosslinked with epichlorohydrin, quaternized with trimethylamine, sold under the name JR 400 by the company Union Carbide | 0.25 g |
| Sodium lauryl ether sulphate (2.2 EO) containing 70% A.M. | 18 g |
| Terpolymer of acrylates, amino (meth)acrylates and $C_{10}$—$C_{30}$ alkyl itaconate, polyoxyethylenated with 20 mol of ethylene oxide, in the form of an aqueous dispersion containing 20% A.M., sold by the company National Starch under the name <<Structure ® Plus>> | 1.5 g |
| Citric acid | 2 g |
| Preserving agents, fragrance | qs |
| Sterilized demineralized water qsp | 100 g |

The pH is adjusted to 5.5 with sodium hydroxide. After using this shampoo, wet sensitized hair is soft and supple and dried hair is smooth and soft and is easy to disentangle. The antidandruff efficacy is good.

| EXAMPLE II: ANTIDANDRUFF SHAMPOO | |
|---|---|
| Sodium chloride | 0.3 g |
| Vitamin B3 or PP: nicotinic amide | qs |
| Sodium N-cocoylamideoethyl-N-ethoxycarboxy-methyl glycinate (38%) | 1.5 g |
| Vitamin B6: pyridoxine hydrochloride | qs |
| Hydroxypropyl guar trimethyl ammonium chloride sold under the name <<Jaguar C 13S>> by the company Meyhall | 0.04 g |
| 1-Hydroxy-4-methyl-6-(2,4,4-trimethylpentyl)-2-pyridone, monoethanolamine salt, sold under the name <<Octopirox>> by the company Hoechst | 0.5 g |
| Polydimethylsiloxane of viscosity 0.3 m².s⁻¹, sold under the name DC200/300,000 by the company Dow Corning | 1.8 g |
| Oxyethylenated lauryl alcohol (2.5 EO) | 0.75 g |
| Fruit extracts in aqueous solution | qs |
| Coconut acit monoisopropanolamide | 2 g |
| Cocoyl amidopropyl betaine as an aqueous 38% solution | 2.7 g |
| Sodium lauryl ether sulphate (2.2 EO) at 70% | 17 g |
| Pyrus Malus (INCI) | qs |
| Distearyl ether | 1.5 g |
| Terpolymer of acrylates, amino (meth)acrylates and $C_{10}$–$C_{30}$ alkyl itaconate, polyoxyethylenated with 20 mol of ethylene oxide, as an aqueous dispersion containing 20% A.M., sold under the name <<Structure ® Plus>> by the company National Starch | 1 g |
| Mixture of linear alcohols (C18/C20/C22) | 1.5 g |
| Fragrance, preserving agents | qs |
| Sterilized demineralized water qsq | 100 g |

The pH is adjusted to 7.5 with citric acid or sodium hydroxide.

After using this shampoo, sensitized wet hair is soft and supple and dried hair is smooth and soft and is easy to disentangle. The antidandruff efficacy is good.

EXAMPLE III: ANTIDANDRUFF SHAMPOO

| EXAMPLE III: ANTIDANDRUFF SHAMPOO | |
|---|---|
| Sodium lauryl ether sulphate (2.2 EO) containing 70% A.M. | 16 g |
| Cocoyl betaine as an aqueous 30% solution, sold under the name <<Dehyton AB 30" by the company Henkel | 6 g |
| Terpolymer of acrylates, amino (meth)acrylates and $C_{10}$–$C_{30}$ alkyl itaconate, polyoxyethylenated with 20 mol of ethylene oxide, in the form of an aqueous dispersion containing 20% A.M., sold by the company National Starch under the name <<Structure ® Plus>> | 1.5 g |
| Coconut acid monoisopropanolamide | 1 g |
| Micronized selenium disulphide powder sold under the name <<Selenium Sulphide USP Micronized>> by the company Ferro Metal | 0.5 g |
| Preserving agents | qs |
| Sterilized demineralized water qsq | 100 g |

The pH is adjusted to 6.5 with citric acid or sodium hydroxide.

After using this shampoo, sensitized wet hair is soft and supple and dried hair is smooth and soft and is easy to disentangle. The antidandruff efficacy is good.

We claim:

1. An antidandruff composition for treating the hair and scalp, comprising at least one antidandruff agent and at least one acrylic terpolymer in a cosmetically acceptable medium, wherein, the at least one antidandruff agent is selected from the group consisting of:

i) benzethonium chloride, benzalkonium chloride, chlorhexidine, chloramine T, chloramine B, 1,3-dibromo-5,5-dimethylhydantoin, 1,3-dichloro-5,5-dimethyl-hydantoin, 3-bromo-1-chloro-5,5-dimethyl-hydantoin, and N-chlorosuccinimide;

ii) 1-hydroxy-2-pyridone derivatives represented by formula (I):

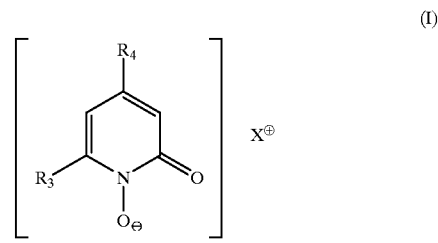

(I)

in which $R_3$ represents an alkyl group containing from 1 to 17 carbon atoms, an alkenyl group containing from 2 to 17 carbon atoms, a cycloalkyl group containing from 5 to 8 carbon atoms or a bicycloalkyl group containing from 7 to 9 carbon atoms; a cycloalkyl (-alkyl) group, an aryl group, an aralkyl group with an alkyl containing from 1 to 4 carbon atoms, an arylalkenyl group with an alkenyl containing from 2 to 4 carbon atoms, an aryloxyalkyl or arylmercaptoalkyl group with an alkyl containing from 1 to 4 carbon atoms, a furylalkenyl group with an alkenyl or a furyl containing from 2 to 4 carbon atoms, an alkoxy group containing from 1 to 4 carbon atoms, a nitro group, a cyano group, or a halogen atom;

$R_4$ represents a hydrogen atom, a $C_1$–$C_4$ alkyl group, a $C_2$–$C_4$ alkenyl group, a halogen atom, a phenyl group, or a benzyl group; and X represents an organic base, an alkali metal ion, an alkaline-earth metal ion or an ammonium ion;

iii) the trihalocarbamides of formula (II) below:

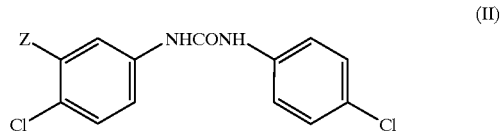

(II)

in which Z represents a halogen atom or a $C_1$–$C_4$ trihaloalkyl group;

iv) triclosan, represented by formula (III)

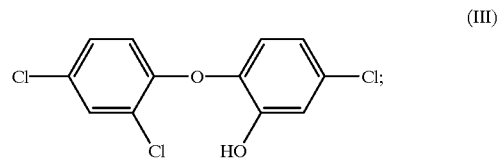

(III)

v) azole compounds;

vi) antifungal polymers;
vii) selenium sulphides;
viii) sulphur in its various forms, cadmium sulphide, allantoin, coal tar or wood tar, undecylenic acid, fumaric acid, and allylamines; and
ix) mixtures thereof; and and wherein, the at least one acrylic terpolymer contains, in amounts based on the total weight of monomers constituting the terpolymer:

acrylate monomer (a), in an amount of 5% to 80% by weight and selected from the group consisting of a $C_1$–$C_6$ alkyl acrylate and a $C_1$–$C_6$ alkyl methacrylate;

monomer (b), in an amount of 5% to 80% by weight and selected from the group consisting of a heterocyclic vinyl compound containing at least one nitrogen or sulphur atom, a (meth)acrylamide, a mono- and di($C_1$–$C_4$)alkylamino($C_1$–$C_4$)alkyl(meth)acrylate, and a mono- and di ($C_1$–$C_4$)alkylamino($C_1$–$C_4$)alkyl(meth)acrylamide; and monomer (c), in an amount of 0.1% to 30% by weight and selected from the group consisting of:
i) a urethane produced by reaction between a monoethylenic unsaturated isocyanate and a nonionic surfactant encompassing a block copolymer of 1,2-butylene oxide and of ethylene oxide containing a $C_{1-4}$ alkoxy end;
ii) a copolymerizable ethylenic unsaturated surfactant monomer obtained by condensing a nonionic surfactant with an α,β-ethylenic unsaturated carboxylic acid or its anhydride;
iii) a urea surfactant monomer produced by reacting a monoethylenic unsaturated monoisocyanate with a nonionic surfactant containing an amine functionality;
iv) a (meth)allyl ether of formula $CH_2=CR_1CH_2OA_mB_nA_pR_2$ in which $R_1$ denotes a hydrogen atom or a methyl group, A denotes a propylenoxy or butylenoxy group, B denotes ethylenoxy, n is equal to zero or denotes an integer less than or equal to 200, m and p denote zero or an integer less than n, and $R_2$ is a hydrophobic group of at least 8 carbon atoms; and
v) a nonionic urethane monomer produced by reacting a monohydric nonionic surfactant with a monoethylenic unsaturated isocyanate.

2. The composition according to claim 1, wherein the terpolymer is present in a proportion of 0.01 to 20% by weight relative to the total weight of the composition.

3. The composition according to claim 1, wherein the monomer (a) is a $C_2$–$C_6$ alkyl acrylate.

4. The composition according to claim 1, wherein the monomer (b) is N,N-dimethylaminoethyl methacrylate, N,N-diethylaminoethyl acrylate, N,N-diethylaminoethyl methacrylate, N-t-butylaminoethyl acrylate, N-t-butylaminoethyl methacrylate, N,N-dimethylaminopropylacrylamide, N,N-dimethylaminopropylmeth-acrylamide, N,N-diethylaminopropylacrylamide, or N,N-diethylaminopropylmethacrylamide.

5. The composition according to claim 1, wherein the monomer (c) is a copolymerizable ethylenic unsaturated surfactant monomer obtained by condensing a nonionic surfactant with itaconic acid.

6. The composition according to claim 1, wherein the acrylic terpolymer consists of acrylates, amino (meth)acrylates, and $C_{10}$–$C_{30}$ alkyl itaconate, polyoxyethylenated with 20 mol of ethylene oxide.

7. The composition according to claim 1, wherein the acrylic terpolymer further contains a crosslinking monomer.

8. The composition according to claim 1, wherein the antidandruff agent is present in a proportion of 0.001% to 10% by weight relative to the total weight of the composition.

9. The composition according to claim 1, further comprising at least one surfactant selected from the group consisting of anionic, amphoteric, nonionic, and cationic surfactants and mixtures thereof.

10. The composition according to claim 9, wherein the anionic surfactants are selected from the group consisting of alkaline salts, magnesium salts, ammonium salts, amine salts, and amino alcohol salts of:

alkyl sulphates, alkyl ether sulphates, alkylamido ether sulphates, alkylaryl polyether sulphates, monoglyceride sulphates, alkyl sulphonates, alkylamide sulphonates, alkylaryl sulphonates, olefin sulphonates, paraffin sulphonates, alkyl sulphosuccinates, alkyl ether sulphosuccinates, alkylamide sulphosuccinates, alkyl sulphosuccinamates, alkyl sulphoacetates, alkyl phosphates, alkyl ether phosphates, acyl sarcosinates, acyl isethionates and N-acyl taurates,
wherein alkyl and acyl is carbon-based chain containing from 8 to 30 carbon atoms,
fatty acid salts of oleic, ricinoleic, palmitic, or stearic acid; coconut oil acid or hydrogenated coconut oil acid; $C_8$–$C_{30}$ acyl lactylates; alkyl D-galactosiduronic acids or salts thereof, polyoxyalkylenated alkyl or alkylaryl ether carboxylic acids or salts thereof; or polyoxyalkylenated alkylamido ether carboxylic acids or salts thereof.

11. The composition according to claim 9, wherein the nonionic surfactants are polyethoxylated, polypropoxylated or polyglycerolated fatty acids or alkylphenols or alcohols having a fatty chain containing 8 to 30 carbon atoms, having between 2 and 50 ethylene oxide or propylene oxide groups, and having between 2 and 30 glycerol groups; copolymers of ethylene oxide and propylene oxide; condensates of ethylene oxide or propylene oxide with fatty alcohols; polyethoxylated fatty amides; polyglycerolated fatty amides; polyethoxylated fatty amines; oxyethylenated fatty acid esters of sorbitan; fatty acid esters of sucrose or of polyethylene glycol; alkylpolyglycosides; or carbamate or amide derivatives of N-alkylglucamines, aldobionamides, or amine oxides.

12. The composition according to claim 9, wherein the amphoteric surfactants are secondary or tertiary aliphatic amine derivatives, in which the aliphatic radical is a linear or branched chain containing 8 to 22 carbon atoms and which contains at least one carboxylate, sulphonate, sulphate, phosphate, or phosphonate water-solubilizing anionic group; ($C_8$–$C_{20}$)alkylbetaines; sulpho-betaines; ($C_8$–$C_{20}$)alkylamido($C_1$–$C_6$)alkylbetaines; or ($C_8$–$C_{20}$)alkylamido($C_1$–$C_6$)alkylsulphobetaines.

13. The composition according to claim 9, wherein the cationic surfactants are optionally polyoxyalkylenated primary, secondary or tertiary fatty amine salts; quaternary ammonium salts; imidazoline derivatives; or cationic amine oxides.

14. The composition according to claim 9, wherein the at least one surfactant is present in a proportion of 0.01% to 50% by weight relative to the total weight of the composition.

15. The composition according to claim 14, wherein the surfactant is present in a proportion of at least 4% by weight relative to the total weight of the composition.

16. The composition according to claim 1, having a pH between 3 and 12.

17. The composition according to claim 1, wherein the cosmetically acceptable medium is water, one or more solvents, or a mixture of water and at least one cosmetically acceptable solvent selected from the group consisting of lower alcohols, alkylene glycols, and polyol ethers.

18. The composition according to claim 1, further comprising at least one volatile or non-volatile silicone selected from the group consisting of:
(i) polyalkylsiloxanes;
(ii) polyarylsiloxanes;
(iii) polyalkylarylsiloxanes;
(iv) silicone gums;
(v) silicone resins;
(vi) organomodified polyorganosiloxanes;
(vii) block copolymers containing a linear polysiloxane-polyalkylene block as a repeating unit;
(viii) grafted silicone polymers, containing a non-silicone organic skeleton;
(ix) grafted silicone polymers, containing a polysiloxane skeleton grafted with non-silicone organic monomers; and
(x) mixtures thereof.

19. The composition according to claim 18, wherein the at least one volatile or non-volatile silicone is present in a proportion between 0.01% and 20% by weight relative to the total weight of the composition.

20. The composition according to claim 1, further comprising at least one cationic polymer selected from the group consisting of proteins and protein hydrolysates, polyamine, polyaminoamide, and polyquaternary ammonium polymers, polyalkyleneimines, polymers containing vinylpyridine units, polymers containing vinylpyridinium units, condensates of polyamines and of epichlorohydrin, polyquaternary ureylenes, and chitin derivatives.

21. The composition according to claim 20, wherein the cationic polymer is present in a proportion between 0.001% and 20% by weight relative to the total weight of the composition.

22. The composition according to claim 1, further comprising at least one cosmetically acceptable adjuvant selected from the group consisting of fragrances, preserving agents, screening agents, sequestering agents, wetting agents, sugars, plant, animal, mineral and synthetic oils, amphoteric polymers, menthol, nicotinate derivatives, agents for preventing hair loss, foam stabilizers, propellants, dyes, ceramides, vitamins, provitamins, acidifying agents, and basifying agents.

23. In a shampoo, lotion, or conditioner the improvement wherein the shampoo, lotion, or conditioner contains the composition as defined in claim 1.

24. A process for treating hair and/or scalp, comprising the step of applying to the hair and/or scalp, when wet or dry, at least one composition as defined in claim 1.

25. The process of claim 24, further comprising the step of rinsing the hair and/or scalp with water after the applying step.

26. The process of claim 25, further comprising the step of leaving the composition on the hair and/or scalp for a period of time before the rinsing step.

27. The composition according to claim 1, wherein Z represents chlorine or $CF_3$.

28. The composition according to claim 1, wherein the azole compounds are selected from the group consisting of climbazole, ketoconazole, clotrinazole, econazole, isoconazole, and miconazole and the antifungal polymers are selected from the group consisting of amphotericin B and nystatin.

29. The composition of claim 1, wherein monomer (a) is present in an amount of 15% to 70% by weight.

30. The composition of claim 1, wherein monomer (a) is present in an amount of 40% to 70% by weight.

31. The composition of claim 1, wherein monomer (b) is present in an amount of 10% to 70% by weight.

32. The composition of claim 1, wherein monomer (b) is present in an amount of 20% to 60% by weight.

33. The composition of claim 1, wherein monomer (c) is present in an amount of 0.1% to 10% by weight.

34. The composition according to claim 1, wherein the terpolymer is present in a proportion of 0.1% to 10% by weight relative to the total weight of the composition.

35. The composition according to claim 1, wherein the monomer (a) is ethyl acrylate.

36. The composition according to claim 1, wherein the monomer (b) is N,N-dimethylaminoethyl methacrylate.

37. The composition according to claim 19, wherein the volatile or non-volatile silicone is present in a proportion between 0.1% and 10% by weight relative to the total weight of the composition.

38. The composition according to 20, wherein:
the proteins or protein hydrolysates are collagen hydrolysates bearing triethylammonium groups, collagen hydrolysates bearing trimethylammonium chloride or trimethylstearylammonium chloride groups, protein hydrolysates bearing on the polypeptide chain quaternary ammonium groups comprising at least one alkyl radical containing from 1 to 18 carbon atoms, or quaternized plant proteins; and
the polyamine, polyaminoamide, or polyquaternary ammonium polymers are
i) quaternized or non-quaternized vinylpyrrolidone/dialkylaminoalkyl acrylate or methacrylate copolymers,
ii) cellulose ether derivatives comprising quaternary ammonium groups,
iii) cationic cellulose derivatives such as cellulose copolymers or cellulose derivatives grafted with a water-soluble quaternary ammonium monomer,
iv) polysaccharides,
v) polymers consisting of piperazinyl units and of divalent alkylene or hydroxyalkylene radicals containing straight or branched chains, optionally interrupted with oxygen, sulphur or nitrogen atoms or with aromatic or heterocyclic rings, or oxidation or quaternization products of said polymers,
vi) water-soluble polyaminoamides,
vii) polyaminoamide derivatives resulting from the condensation of polyalkylene polyamines with polycarboxylic acids followed by alkylation with bifunctional agents,
viii) polymers obtained by reacting a polyalkylene polyamine comprising two primary amine groups and at least one secondary amine group with a dicarboxylic acid selected from the group consisting of diglycolic acid and saturated aliphatic dicarboxylic acids containing from 3 to 8 carbon atoms,
ix) cyclopolymers of methyldiallylamine or of dimethyldiallylammonium,
x) diquaternary ammonium polymers,
xi) polyquaternary ammonium polymers, xii) homopolymers or copolymers derived from acrylic or methacrylic acids and comprising $CH_2-CHR_a-CO-O-A_1-NR_eR_f$, $CH_2-CHR_a-CO-O-A_1-N^+R_bR_cR_d\ X^-$, and/or $CH_2-CHR_a-CO-NH-A_1-N^+R_bR_cR_d\ X^-$ units, in which $R_a$ independently denotes H or $CH_3$, $A_1$ independently denotes a linear or branched alkyl group of 1 to 6 carbon atoms or a hydroxyalkyl group of 1 to 4 carbon atoms, $R_b$, $R_c$, and $R_d$, which may be identical or different, independently denote an alkyl group of 1 to 18 carbon atoms or a benzyl radical, $R_e$ and $R_f$ represent a hydrogen atom or an alkyl group of 1 to 6 carbon atoms, $X^-$ denotes an anion, xiii) quaternary polymers of vinylpyrrolidone and of vinylimidazole, xiv) polyethylene glycol tallow polyamine, or xv) crosslinked methacryloyloxyethyltrimethylammonium chloride polymers.

* * * * *